(12) United States Patent
Fiedler et al.

(10) Patent No.: US 11,234,718 B2
(45) Date of Patent: Feb. 1, 2022

(54) GUIDED MILLING DEVICE FOR PROSTHETIC SURGERY

(71) Applicant: LIMACORPORATE S.P.A, San Daniele del Friuli (IT)

(72) Inventors: Christoph Fiedler, Diekhof (DE); Massimo Ceconi, Travesio (IT); Nicola Del Negro, San Daniele del Friuli (IT)

(73) Assignee: LIMACORPORATE S.P.A, San Daniele del Friuli (IT)

( * ) Notice: Subject to any disclaimer, the term of this patent is extended or adjusted under 35 U.S.C. 154(b) by 0 days.

(21) Appl. No.: 17/206,625

(22) Filed: Mar. 19, 2021

(65) Prior Publication Data

US 2021/0290255 A1 Sep. 23, 2021

(30) Foreign Application Priority Data

Mar. 19, 2020 (IT) ........................ 102020000005947

(51) Int. Cl.
*A61B 17/00* (2006.01)
*A61B 17/16* (2006.01)
*A61B 17/17* (2006.01)
*A61F 2/46* (2006.01)
*A61F 2/40* (2006.01)

(52) U.S. Cl.
CPC ...... *A61B 17/1684* (2013.01); *A61B 17/1778* (2016.11); *A61F 2/4081* (2013.01); *A61F 2/4612* (2013.01); *A61B 2017/00424* (2013.01); *A61B 2017/00477* (2013.01)

(58) Field of Classification Search
CPC combination set(s) only.
See application file for complete search history.

(56) References Cited

U.S. PATENT DOCUMENTS

2021/0100562 A1\* 4/2021 Rodriguez ......... A61B 17/1615

\* cited by examiner

*Primary Examiner* — Sameh R Boles
(74) *Attorney, Agent, or Firm* — Calfee, Halter & Griswold LLP

(57) ABSTRACT

Milling device for prosthetic surgery comprising a milling tool rotating about a milling axis, and a handling body. The handling body is provided with a drive rotating rod which develops along a longitudinal axis of linear rotation and is connected to the milling tool in order to make the milling tool rotate about the milling axis.

21 Claims, 12 Drawing Sheets

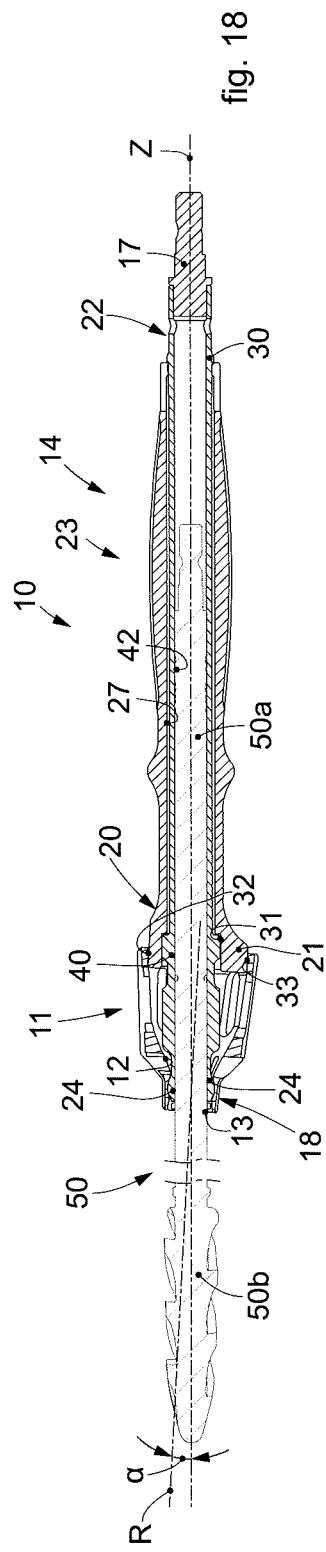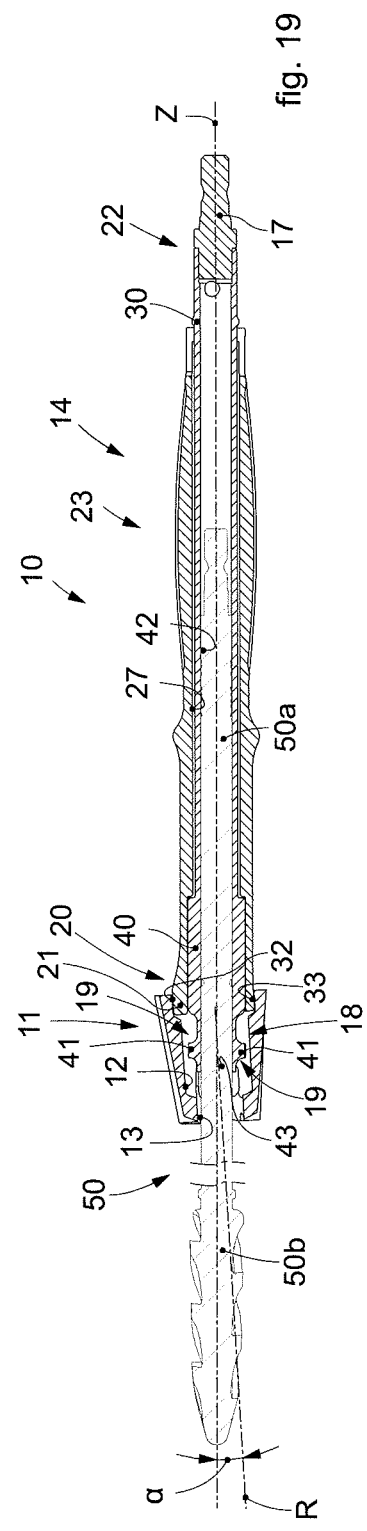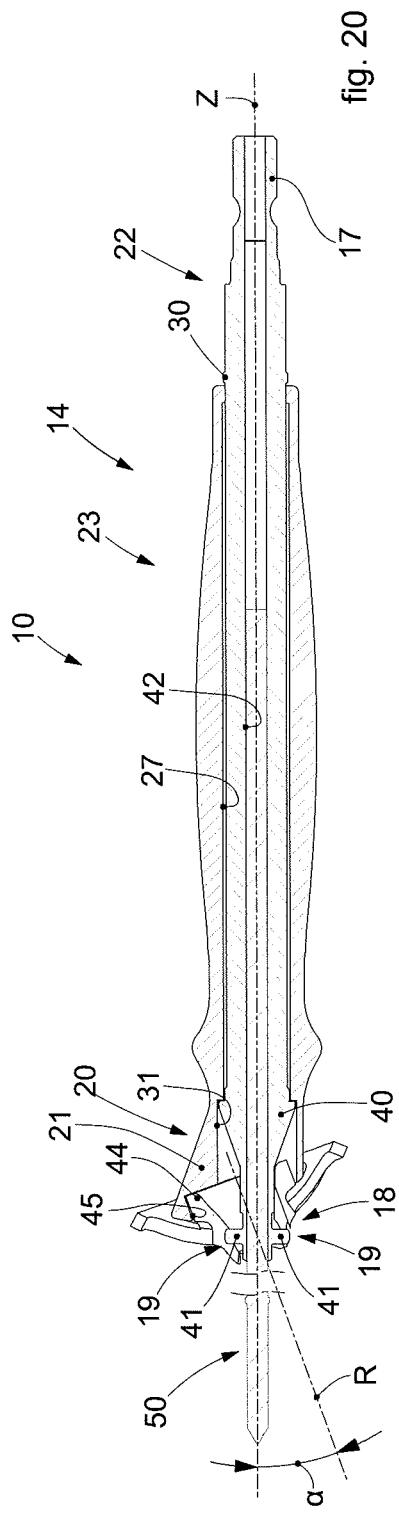

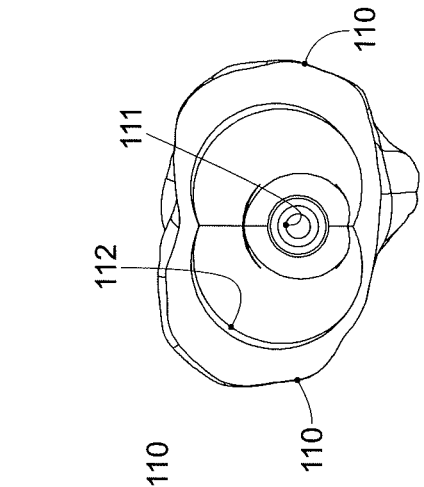
fig. 29
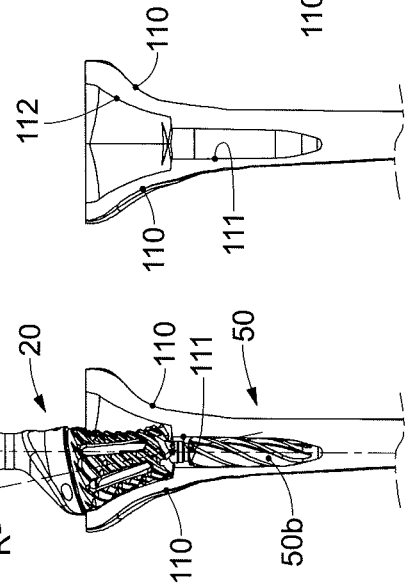
fig. 28
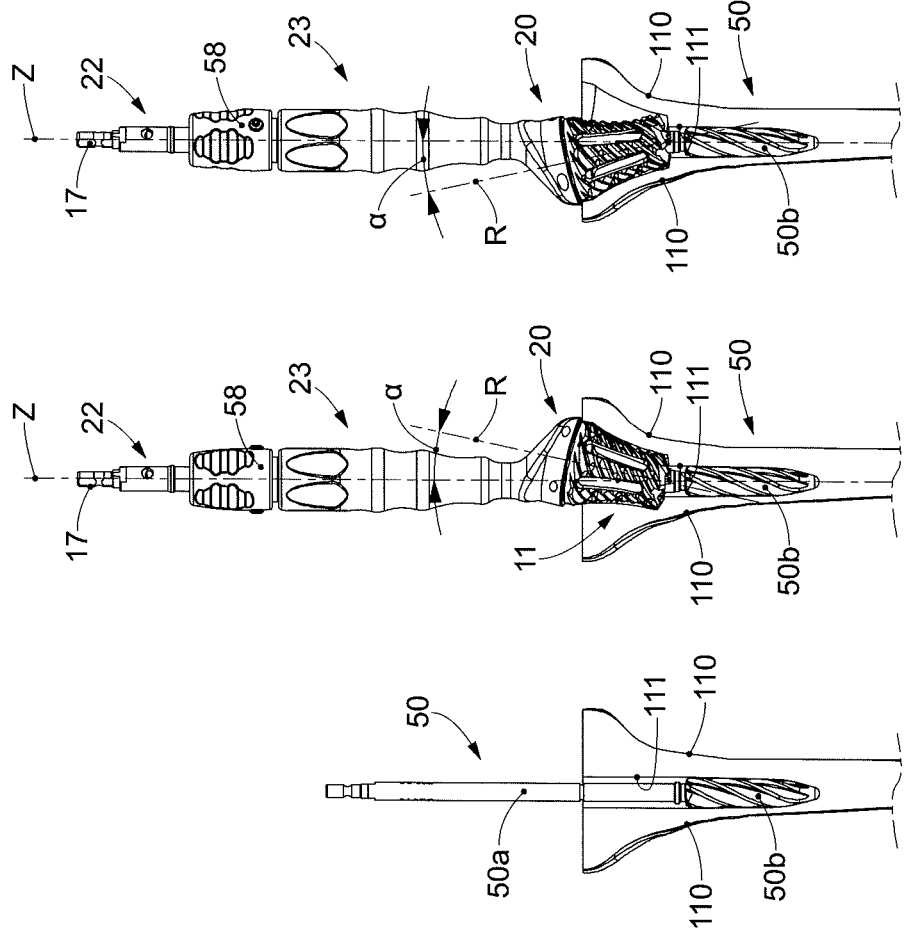
fig. 27
fig. 26
fig. 25

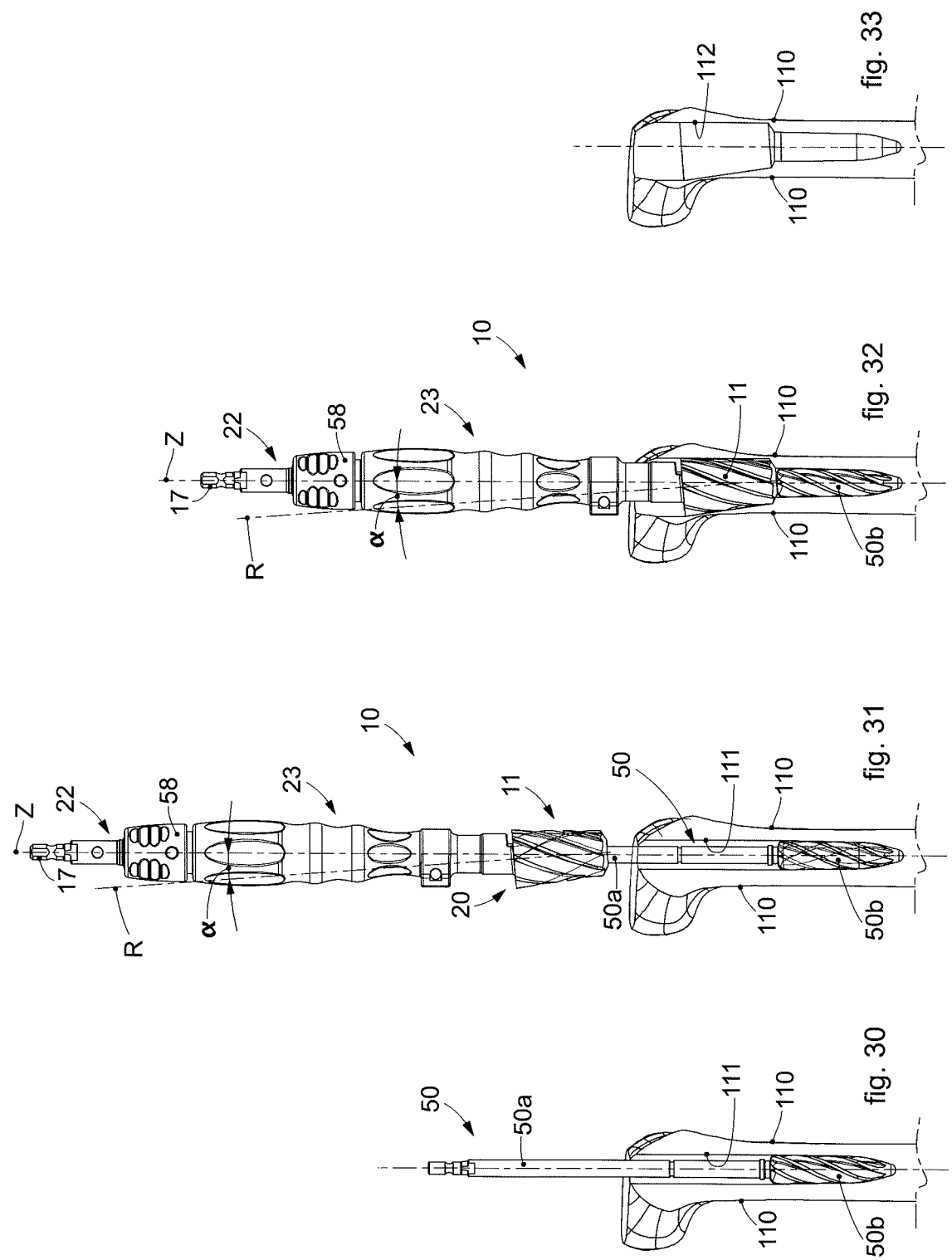

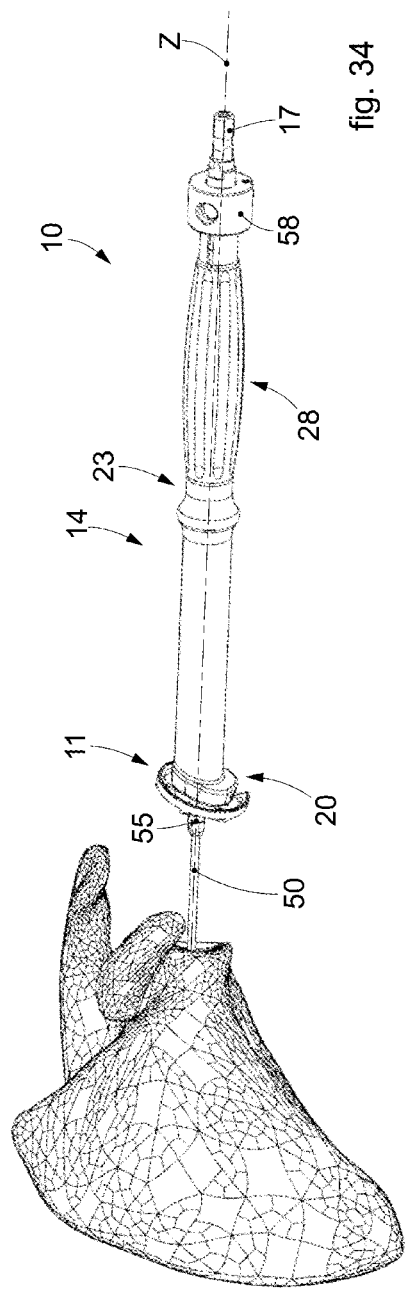
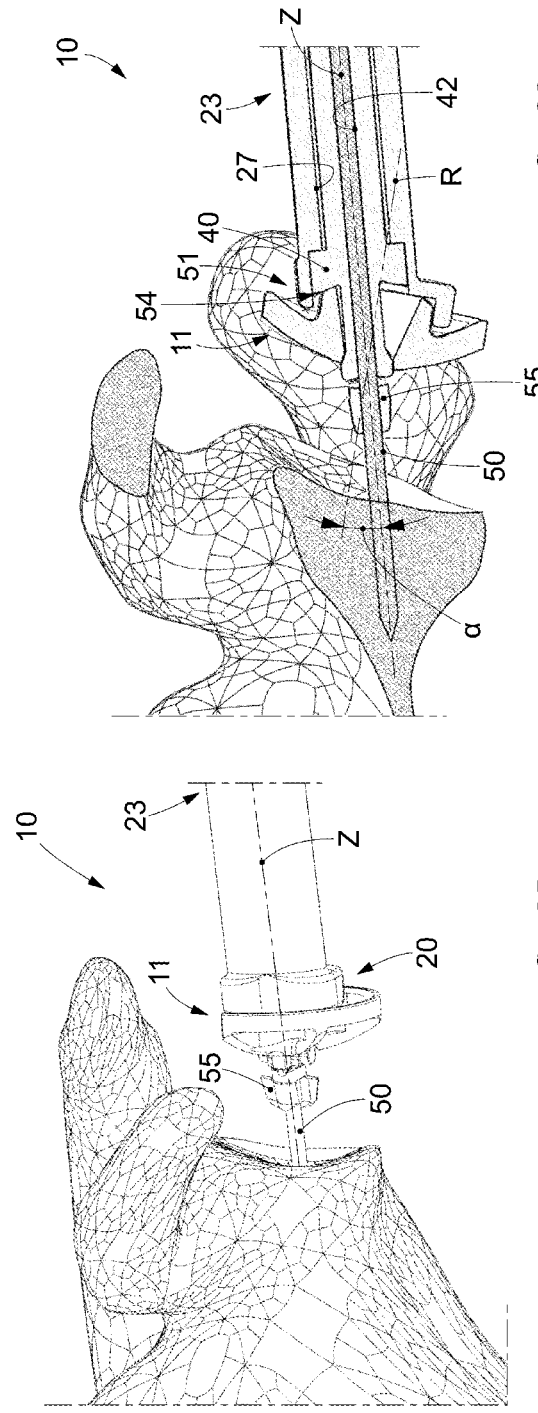
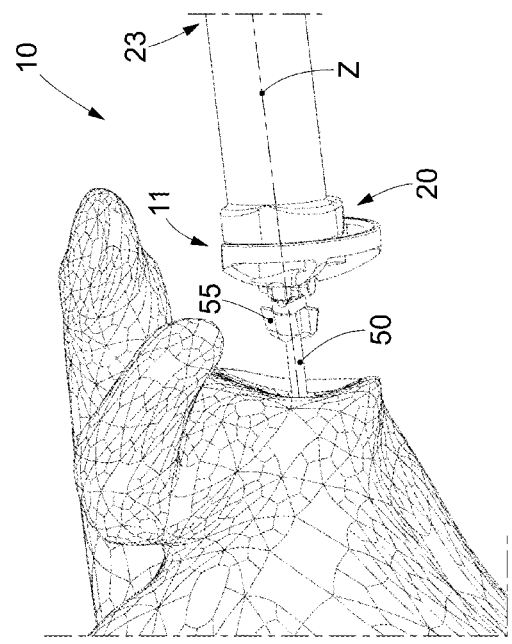
fig. 34
fig. 35
fig. 36

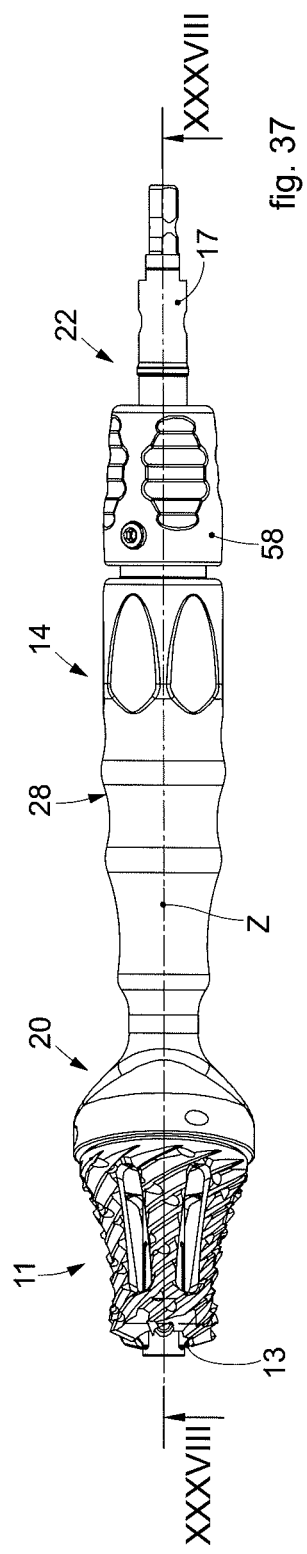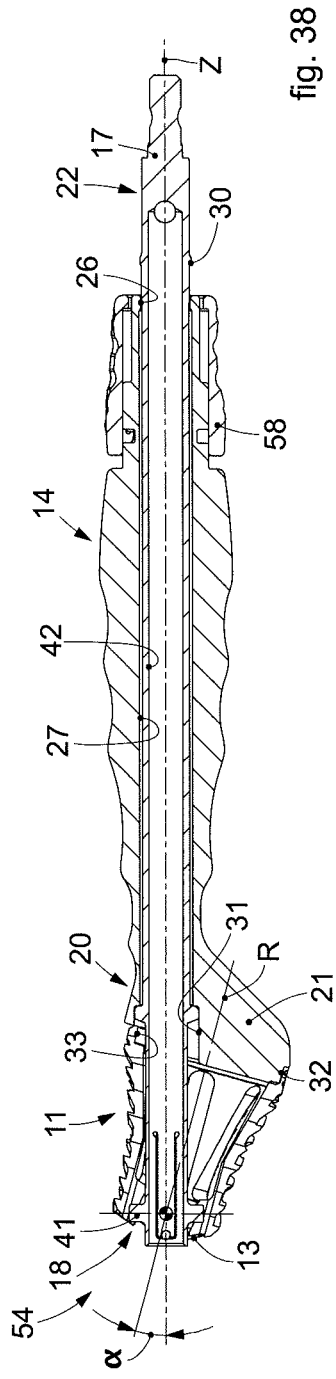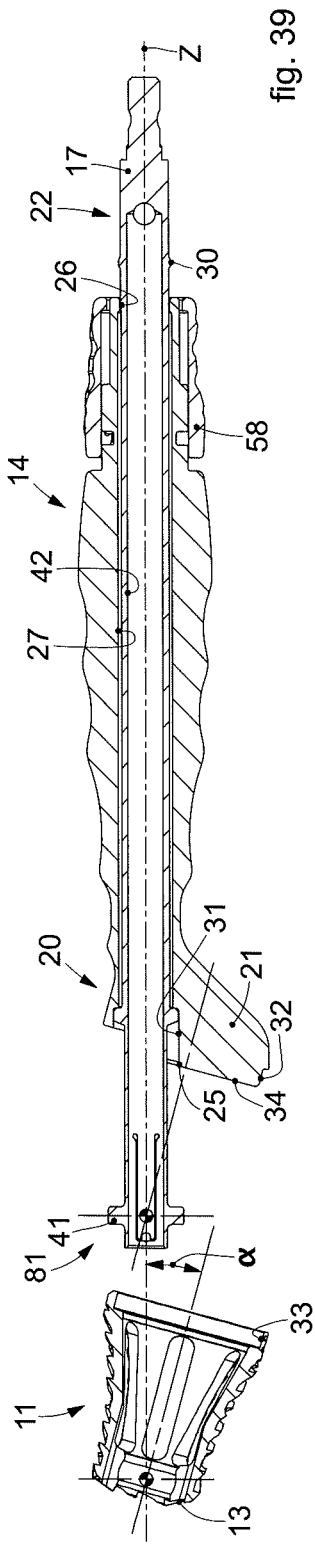

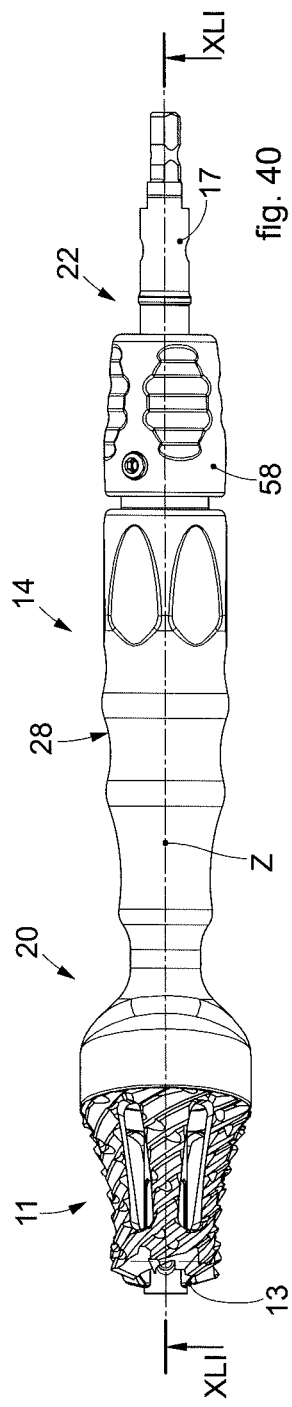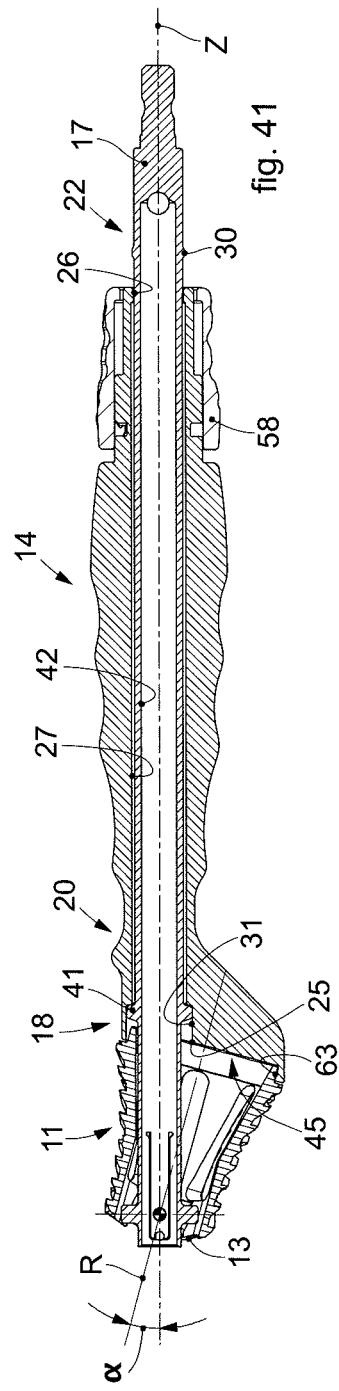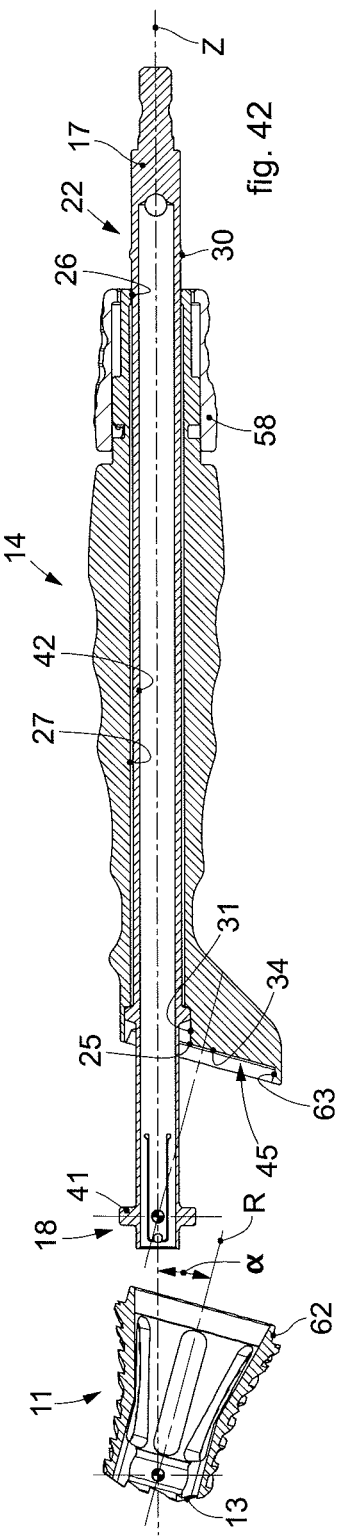

GUIDED MILLING DEVICE FOR PROSTHETIC SURGERY

FIELD OF THE INVENTION

The present invention concerns a guided milling device for prosthetic surgery suitable for the preparation of seatings for bone fillers or for the preparation of housing seatings in the bone for a prosthesis.

In particular, the milling device is particularly suitable for making seatings for bone fillers for a knee prosthesis or for the preparation of a bone seating for a shoulder joint prosthesis, also called humeral prosthesis, or for a hip prosthesis.

BACKGROUND OF THE INVENTION

It is known that, in orthopedic surgery for the implantation of a prosthesis, when it is required to prepare a seating for a bone filler or prepare a housing seating for a prosthesis, it is necessary to make a hole in the bone and/or a milling operation to make the seating with the desired profile.

Often, in fact, congenital or traumatic degenerative diseases, for example primary arthrosis or secondary arthrosis, due to trauma or caused by infections, rheumatoid arthritis, inflammatory arthritis, osteonecrosis, or bone tumors, or other similar problems, require implantation of a prosthesis able to reproduce, overall, a movement similar to that of the healthy joint.

It is also known that when, due to the pathologies as above, the spongy part of the bone is unable to support the prosthesis, it is necessary to create appropriate bone seatings for the implantation of a bone or metal filler that acts as a support for the prosthesis. This problem can become critical especially for knee prostheses and hip and shoulder prostheses.

The knee prosthesis typically comprises a femoral component, which is attached to the distal end of the femur, and a tibial component, which is attached to the proximal end of the tibia.

Especially in the case where it is necessary to recondition a previously implanted knee prosthesis, the creation of a bone seating, for the application of suitable support cones, first requires that a hole is made, with one or more boring devices of increasing diameter, and subsequently that the hole is shaped with a suitable milling device.

For this purpose, milling devices are known, which can be used during prosthetic surgery for the preparation of said seatings.

These milling devices typically comprise a handling body provided with a rotating rod which develops along a longitudinal axis, substantially coinciding with the axis of the intra-medullary canal, depending on the case, of the tibia or femur, and provided with a proximal end which has a connector to a drive member and a distal end connected to a milling tool, made to rotate by the drive member.

Given that both tibia and femur have an asymmetrical elongated conformation, one of the main problems encountered during the preparation of a bone seating is to avoid perforation of the cortical zone of the tibial and femoral bone.

One of the disadvantages of known milling devices is that they are configured to shape the bone seating in the direction of a milling axis which substantially coincides with the axis of the intra-medullary canal, and consequently with the longitudinal axis around which the rotating rod is driven, depending on the case, of the tibia or femur; such devices are therefore not able to follow the specific anatomy of the tibial and femoral bone.

To help the surgeon in the milling operation, the milling device often comprises, or is combined with, a guide rod which is previously inserted into the intra-medullary canal. The guide rod is slidably positioned inside the milling device along the longitudinal axis, and therefore is also coaxial to the milling axis. Although this solution allows the surgeon to follow a desired milling direction in a guided way, it does not allow to incline the milling axis with respect to the longitudinal axis and therefore to the axis of the intra-medullary canal, with the consequent risk of damaging, in particular perforating, the cortical zone. This risk occurs in particular when the milling diameter is increased to make the implant seating.

Sometimes, to avoid perforation of the cortical zone, the surgeon is therefore obliged to make bone seatings of a limited size which may, however, not be sufficient to guarantee adequate joint stability of the prosthesis, especially in the case where previous prostheses implants have damaged or otherwise rendered unusable an extended zone of the spongy part of the bone, or the removal of the previous implant has created significant bone loss or there is degeneration or lack of bone.

There is therefore a need to perfect a guided milling device for prosthetic surgery which can overcome at least one of the disadvantages of the state of the art.

In particular, one purpose of the present invention is to provide a guided milling device for prosthetic surgery which is able to perform milling operations while avoiding damage to the cortical zone of the bone.

Another purpose of the present invention is to provide a guided milling device for prosthetic surgery which is able to obtain a stable milling with respect to a milling axis different from the axis of the intra-medullary canal or different from the axis of the guide rod that is inserted into it.

Another purpose of the present invention is to provide a guided milling device for prosthetic surgery which is simple to use and which consists of a limited number of components.

Another purpose of the present invention is to provide a guided milling device for prosthetic surgery which is simple to assemble, in order to carry out the surgical operation, and to disassemble, in order to carry out cleaning and sterilization thereof.

The Applicant has studied, tested and embodied the present invention to overcome the shortcomings of the state of the art and to obtain these and other purposes and advantages.

SUMMARY OF THE INVENTION

The present invention is set forth and characterized in the independent claim. The dependent claims describe other characteristics of the present invention or variants to the main inventive idea.

In accordance with the above purposes, the guided milling device for prosthetic surgery comprises a milling tool rotating about a milling axis, and a handling body having a drive rotating rod which develops along a longitudinal axis of linear rotation. The rotating rod is connected to the milling tool in order to make the milling tool rotate about the milling axis.

The rotating rod is internally hollow and has a guide channel parallel to the longitudinal axis and in which a guide rod is positioned coaxially in a slidable manner, able to be positioned so as to extend beyond the milling tool along the longitudinal axis.

The milling axis is inclined with respect to the longitudinal axis, so that the milling tool is disposed inclined with respect to the rotating rod and also with respect to the guide rod.

In some embodiments, the point of intersection of the milling axis and the longitudinal axis falls outside the milling tool.

BRIEF DESCRIPTION OF THE DRAWINGS

These and other aspects, characteristics and advantages of the present invention will become apparent from the following description of some embodiments, given as a non-restrictive example with reference to the attached drawings wherein:

FIG. 18 shows a section view of a milling device for prosthetic surgery, in particular for application to the tibial bone, in which the guide rod is shown;

FIG. 19 shows a section view of a milling device for prosthetic surgery, in particular for application to the femoral bone, in which the guide rod is shown;

FIG. 20 shows a section view of a milling device for prosthetic surgery, in particular for application to the shoulder joint, in particular for the glenoid, in which the guide rod is shown;

FIGS. 25-29 show a possible operating sequence of use of a milling tool for surgical application to the tibial bone;

FIGS. 30-33 show a possible operating sequence of use of a milling tool for surgical application to the femoral bone;

FIGS. 34-36 show a possible operating sequence of use of a milling tool for application to the shoulder joint, in particular for the glenoid cavity;

FIG. 37 shows a top view of a milling device for prosthetic surgery, in particular for application to the tibial bone, in accordance with other embodiments described here;

FIG. 38 is a section along line XXXVIII-XXXVIII of FIG. 37;

FIG. 39 is a representation of FIG. 38 in which the milling tool is shown separate;

FIG. 40 shows a top view of a milling device for prosthetic surgery, in particular for application to the tibial bone, in accordance with other embodiments described here;

FIG. 41 is a section along line XLI-XLI of FIG. 40;

FIG. 42 is a representation of FIG. 41 in which the milling tool is shown separate;

To facilitate comprehension, the same reference numbers have been used, where possible, to identify identical common elements in the drawings. It is understood that elements and characteristics of one embodiment can conveniently be incorporated into other embodiments without further clarifications.

DETAILED DESCRIPTION OF SOME EMBODIMENTS

Figure 1:
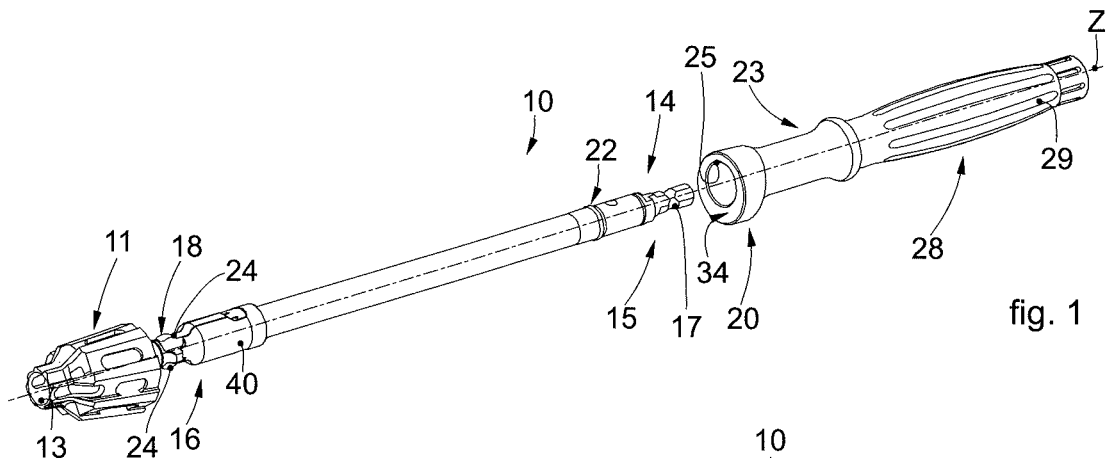
FIG. 1 shows an exploded perspective view of a milling device for prosthetic surgery, in particular for application to the tibial bone, in accordance with some embodiments described here.

We will now refer in detail to the various embodiments of the invention, of which one or more examples are shown in the attached drawings. Each example is supplied by way of illustration of the invention and shall not be understood as a limitation thereof. For example, the characteristics shown or described insomuch as they are part of one embodiment can be adopted on, or in association with, other embodiments to produce another embodiment. It is understood that the present invention shall include all such modifications and variants.

Before describing these embodiments, we must also clarify that the present description is not limited in its application to details of the construction and disposition of the components as described in the following description using the attached drawings. The present description can provide other embodiments and can be obtained or executed in various other ways. We must also clarify that the phraseology and terminology used here is for the purposes of description only, and cannot be considered as limitative.

Embodiments described using the attached drawings concern a guided milling device for prosthetic surgery, indicated as a whole with reference number 10 in the attached drawings.

With particular reference to the attached drawings, FIGS. 1-9, 37-42 concern a guided milling device 10 suitable for making seatings for bone fillers for the tibial bone, FIGS. 10-13, 43-46 concern a milling device 10 suitable for making seatings for bone fillers for the femoral bone and FIGS. 14-17 concern a milling device 10 suitable for making seatings for a shoulder joint prosthesis, also called humeral prosthesis. FIGS. 18-20 show embodiments of the milling device 10 respectively configured for the preparation of a seating in the tibial bone, in the femoral bone and in the shoulder joint, in which a guide rod 50 is slidingly associated. FIGS. 21-24 concern another embodiment of the milling device 10 suitable for making seatings for a shoulder joint prosthesis, in particular for the glenoid, FIGS. 25-29 and 30-33 concern the use for milling of the tibial and femoral bone respectively.

The guided milling device for prosthetic surgery 10, hereafter device 10, comprises a milling tool 11, rotating about a milling axis R, and a handling body 14 having a drive rotating rod 22 which develops along a longitudinal axis Z of linear rotation. The rotating rod 22 is connected to the milling tool 11 to make the milling tool 11 rotate about the milling axis R. This longitudinal axis Z is favorably a linear axis.

In accordance with some embodiments described here, the rotating rod 22 is cannulated, that is it is internally hollow and has a guide channel 42 parallel to the longitudinal axis Z and suitable to house a guide or reference rod 50 necessary to axially position the device 10 in the desired milling position during the surgical operation.

The guide rod 50 is coaxially housed in the guide channel 42 and is slidably positioned therein to extend beyond the milling tool 11 along the longitudinal axis Z. The amount by which the guide rod 50 extends beyond the milling tool 11 is coordinated and aimed at the insertion of the guide rod 50 into the intra medullary canal in order to guide the milling operation (see for example FIGS. 21-23, 25-27, 30-32, 34-36).

In accordance with the present invention, the milling axis R is inclined with respect to the longitudinal axis Z, so that the milling tool 11 is disposed inclined with respect to the rotating rod 22 and also with respect to the guide rod 50.

Consequently, according to the present invention, since the guide rod 50 is inserted into the guide channel 42 along the longitudinal axis Z, it follows that the milling axis R is actually also inclined with respect to such guide channel 42 and therefore to the guide rod 50, when in use.

In accordance with some embodiments, the guide rod 50 has, at least in the proximal part, a transverse size, in particular a diameter, which is smaller than the transverse size of the guide channel 42, so that it can be inserted in the latter, but with limited transverse play. In the distal part, on the other hand, the guide rod 50 can have a diameter which is also larger, which is a function of the anatomical canal.

The guide rod 50, or at least a guide portion 50a thereof, can have a shorter length than the length of the guide channel 42 measured along the longitudinal axis Z.

The milling tool 11, although it is guided along the guide rod 50 and therefore along the longitudinal axis Z, allows to define a bone seating having a development along an axis that is different to that of the guide rod 50, that is along the milling axis R inclined with respect to the longitudinal axis Z.

In accordance with possible embodiments, the guide rod 50 can be a reference pin, a more or less thin rigid shaft, a so-called Kirschner wire or "lead wire", for example in the case of a shoulder joint, or similar guide element. Depending on the applications, the guide rod 50 can have a shaped tip, with teeth, coils or other elements, to act as a reamer mean, for example in the event it is used for the tibial or femoral intra-medullary canal.

In particular, in accordance with some embodiments, shown in FIGS. 18-19, at least in the case of a milling device 10 for the femoral and/or tibial bone, the guide rod 50 can generally be a reaming device which, suitably driven by a motorized or manual drive mean, is used before the device 10 in order to create a first hole, or first holes of increasing diameters in the intra-medullary canal. Once the suitable diameter of the hole has been reached, the guide rod 50 is left in the intra-medullary canal where the hole was created and is released from the drive mean. After that, the device 10 is prepared so that the guide rod 50 is inserted into the guide channel 42 and acts as an axial guide during the milling operation. In the example described here, the guide rod 50 comprises a guide portion 50a able to cooperate with the guide channel 42, and a reaming portion 50b which always remains outside the milling tool 11.

In accordance with the embodiment shown in FIG. 20, the guide rod 50 is configured as a guide wire, also called Kirschner wire or k-wire, or it can also be a so-called "lead wire". In fact, in the case of the shoulder joint, the intra-medullary canal has a reduced cross-section compared to the tibial or femoral bone and it is not possible to use a reaming tool as in the applications to the femoral and tibial bones. As shown in FIGS. 34-36, the milling tool 11 is guided and advances along the wire, which in this case acts as a guide rod 50, previously inserted and aligned along the final axis of the prosthetic implant. At the same time, the milling tool 11 is able to rotate and prepare a seating, for example of a spherical shape, oriented along an axis—the milling axis R—that is inclined with respect to that of the wire which acts as a guide rod 50—coinciding with the longitudinal axis Z. In this specific case, the inclined axis along which the seating being prepared is oriented, defined by the milling axis R, is an axis essentially orthogonal to the eroded surface of the glenoid.

In accordance with some embodiments, the handling body 14 comprises an angular positioning assembly 51 configured to define the inclined disposition of the milling tool 11 with respect to the guide rod 50 and to the rotating rod 22, as described above.

The angular positioning assembly 51 comprises articulation means 54, to connect the milling tool 11 to the rotating rod 22 in an articulated manner, and a positioning member 20, disposed on a tubular handle 23 of the handling body 14.

In accordance with some embodiments, the articulation means 54 can comprise an angular joint 18 (see for example FIGS. 1, 10 and 14), disposed on one end of the rotating rod 22, or, or in addition, a pair of articulated surfaces 52, 53 (see for example FIGS. 23-24) respectively defined on the rotating rod 22 and on an internal part of the milling tool 11, so as to configure a spherical joint. Favorably, the angular joint 18 lies on the longitudinal axis Z. In particular, the angular joint 18 essentially lies on the intersection of the longitudinal axis Z and the milling axis R.

Figure 8:
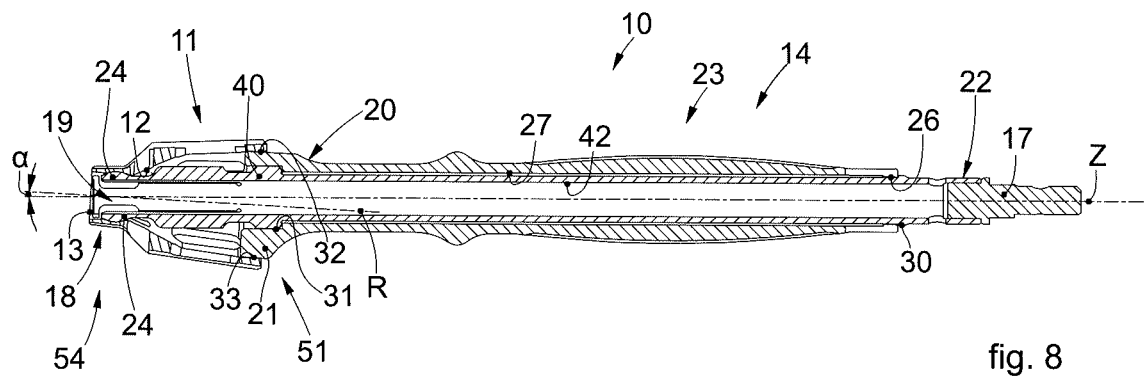
FIG. 8 is a section along line VIII-VIII of FIG. 6.
Figure 9:
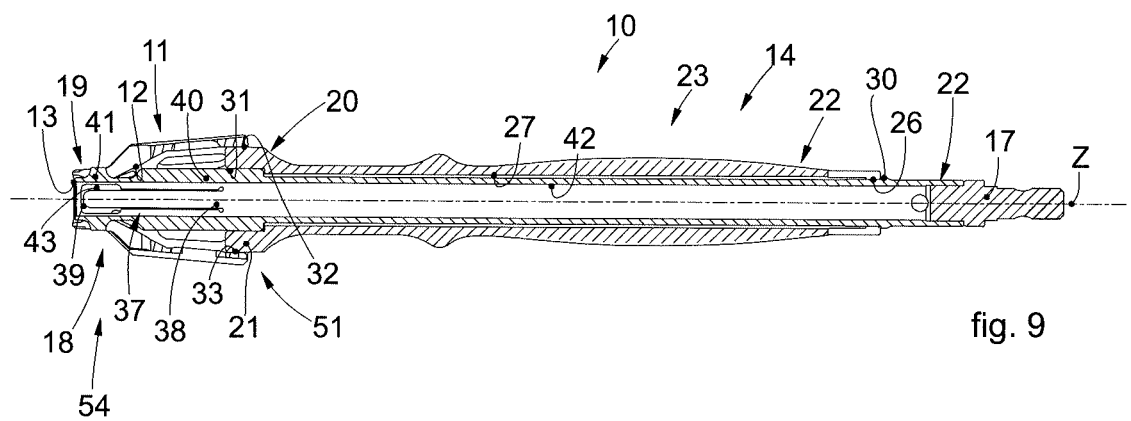
FIG. 9 is a section along line IX-IX of FIG. 7.
Figure 23:
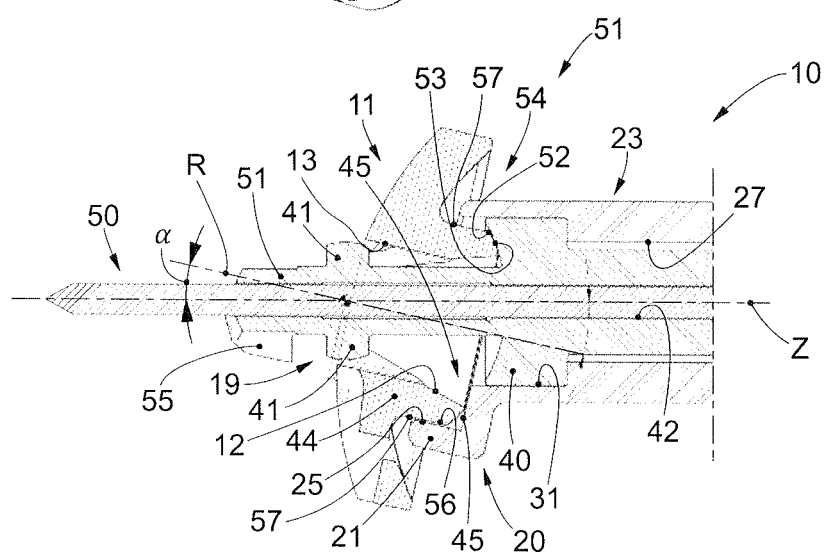
FIG. 23 is a section view of FIG. 22.
Figure 24:
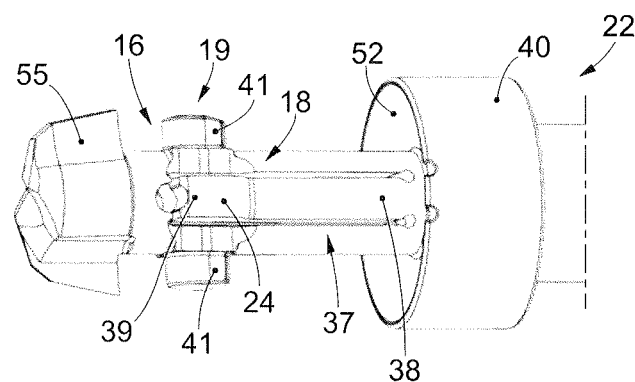
FIG. 24 shows an enlarged detail of the rotating rod present in FIGS. 21-23.
Figure 43:
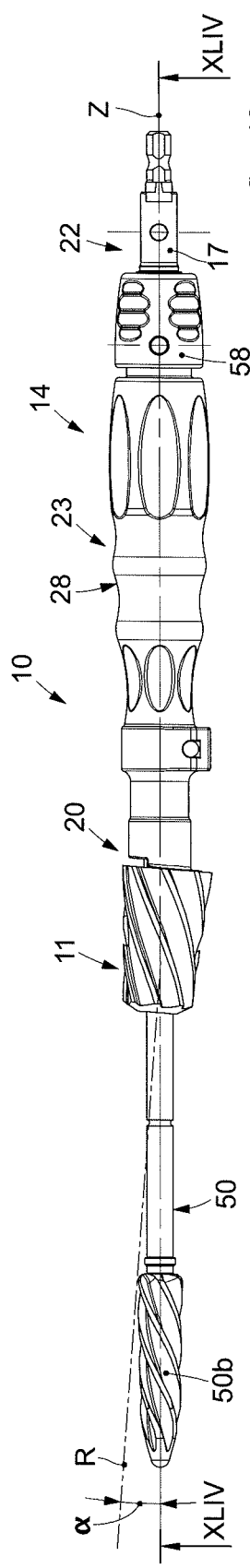
FIG. 43 shows a top view of a milling device for prosthetic surgery, in particular for application to the femoral bone, in accordance with other embodiments described here, in which the guide rod is shown.
Figure 44:
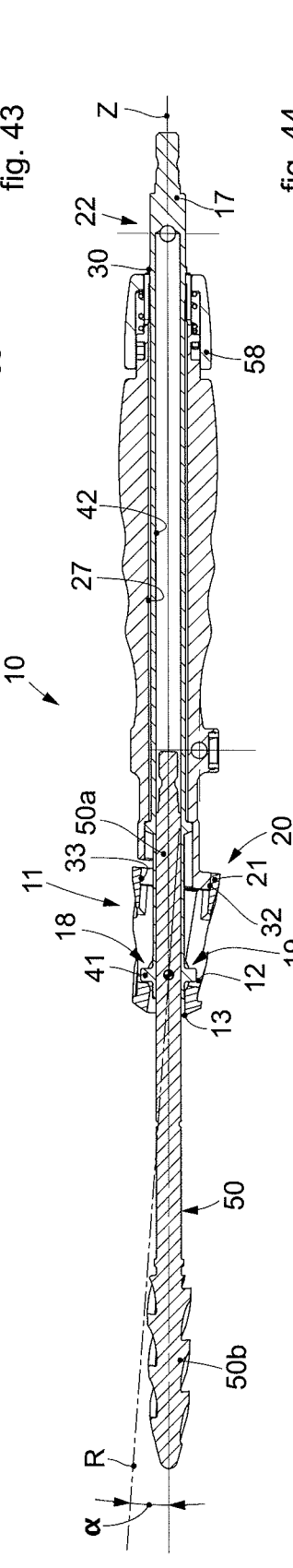
FIG. 44 is a section along line XLIV-XLIV of FIG. 43.
Figure 45:
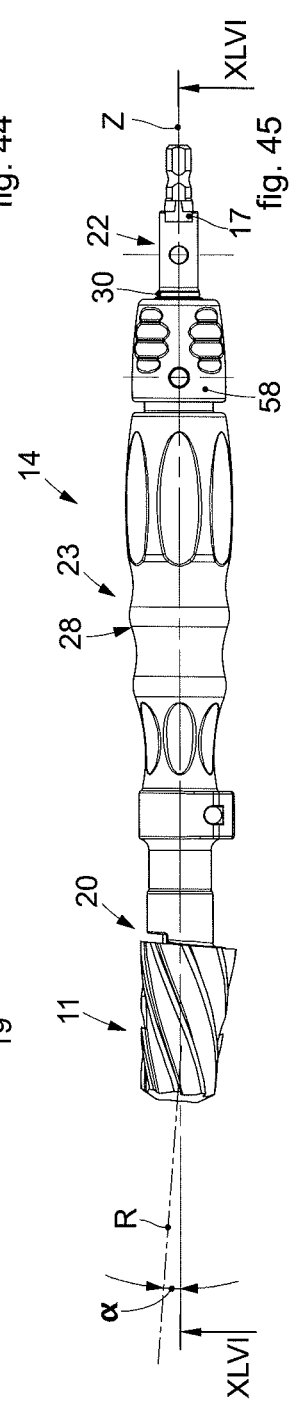
FIG. 45 shows a top view of a milling device for prosthetic surgery, in particular for application to the femoral bone, in accordance with other embodiments described here.
Figure 46:
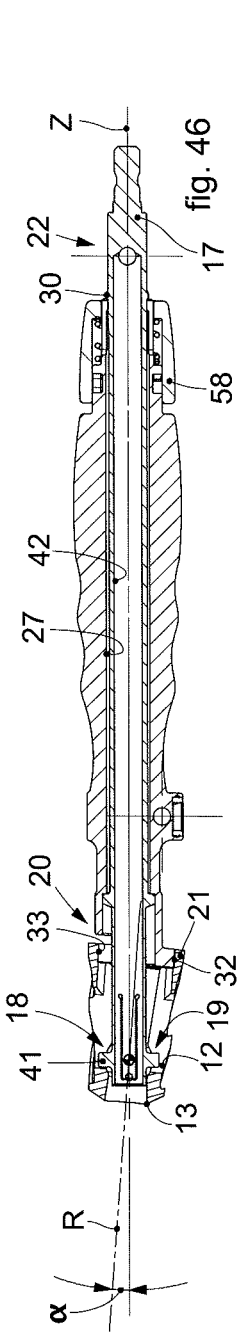
FIG. 46 is a section along line XLVI-XLVI of FIG. 45.

For example, the angular joint 18 can be completely contained inside the milling tool 11, see for example FIGS. 8-9, or be partly outside and partly inside the milling tool 11, see for example FIG. 23.

The articulation means 54 allow to selectively define a plurality of inclined positions of the milling tool 11 with respect to the longitudinal axis Z.

The positioning member 20 comprises a stabilizing body 21 disposed eccentric with respect to the longitudinal axis Z and configured to cooperate with the milling tool 11 so as to selectively define, from among the plurality of inclined positions as above, a single specific stable inclined position of the milling tool 11 with respect to the longitudinal axis Z.

On the basis of the conformation of the stabilizing body 21 and the reciprocal cooperation with the milling tool 11, it is therefore possible to determine the desired angular position, which, once selected, is used to carry out the milling with the chosen angle of inclination of the milling axis R.

The specific stable inclined position allows the milling tool 11 to rotate with respect to the milling axis R.

The milling axis R is inclined with respect to the longitudinal axis Z of rotation of the rotating rod 22 by an angle of inclination $\alpha$ which varies according to the surgical application (application to the tibial bone, to the femoral bone or to the shoulder joint). Therefore it can be said that the milling tool 11 is inclined with respect to the rotating rod 22 and with respect to the guide rod 50.

In particular, the positioning member 20 defines the angle of inclination $\alpha$ so that when the rotating rod 22 rotates with respect to the longitudinal axis Z, the milling tool 11 rotates with respect to the milling axis R.

Figure 5:
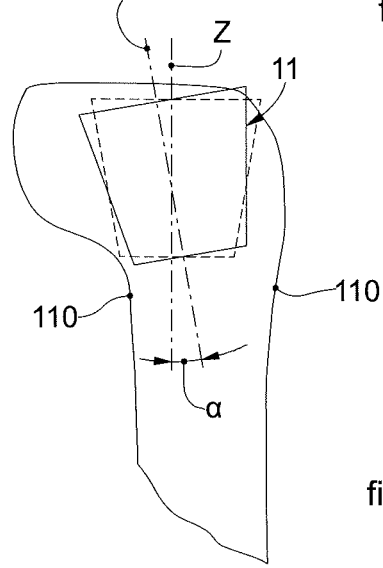
FIG. 5 shows a schematic view of a possible application of the milling device for prosthetic surgery in accordance with some embodiments described here.
Figure 6:
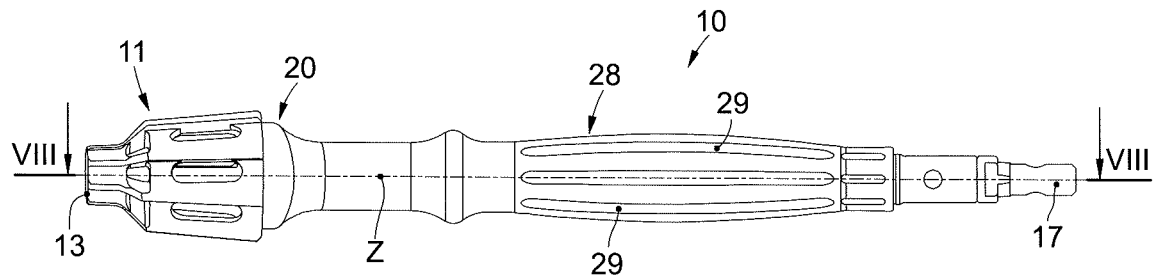
FIG. 6 shows a lateral view of a milling device for prosthetic surgery, in particular for application to the tibial bone, in accordance with some embodiments described here.
Figure 7:
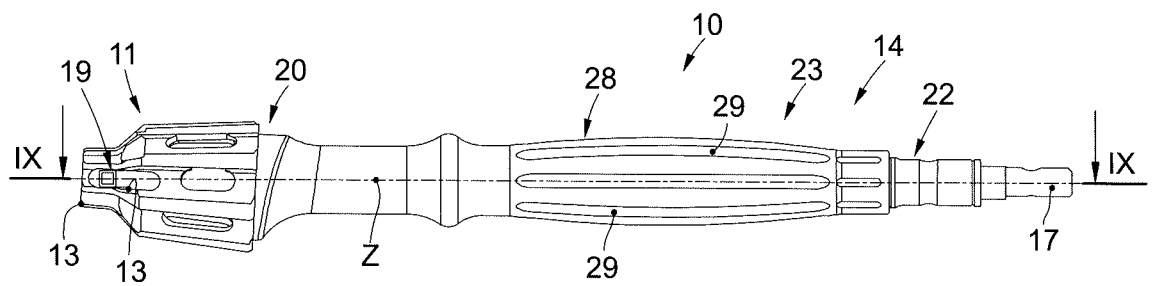
FIG. 7 is another lateral view of FIG. 6.

As shown schematically in FIG. 5, with this configuration of the device 10 it is possible to create a bone seating without damaging the cortical zone 110 of the bone. In fact, while overall the device 10 is used so that the longitudinal axis Z is substantially orthogonal to the tibial resection, that is substantially parallel to the intra-medullary canal, this device 10 shapes the bone seating as above with respect to the angle of inclination $\alpha$ that corresponds to the specific stable inclined position. Optionally, the milling tool 11 can have the profile of a solid of revolution, obtained rotating a desired curve, which for example approximates the internal geometry of the tibia or femur. In particular, a known milling device is schematically shown in a dashed line, the device 10 in accordance with the embodiments described here is shown in a continuous line. Evidently, the known milling device comes much closer to the cortical zone 110, with the risk of damaging it by perforating it.

In addition, this allows the user to create a deeper bone seating, being able to ensure, especially in the case of severe degeneration of the spongy part of the bone, a suitable joint stability of the prosthesis.

The milling tool 11 has a concave coupling seating 12 having a polar coupling aperture 13, through which the guide rod 50 is made through. The guide rod 50 therefore has a smaller transverse size than the transverse size of the polar coupling aperture 13.

The rotating rod 22 is provided with a distal end 16 connected to the milling tool 11 inside the concave coupling seating 12 in correspondence with the polar coupling aperture 13, and a proximal end 15 which has a tang 17 for attachment to a drive member to make the milling tool 11 rotate about the milling axis R. The distal end 16 is open to allow the guide rod 50 access to the guide channel 42.

Here and hereafter, the relative terms "proximal" and "distal" when they describe the rotating rod 22 of the milling device 10 are defined with reference to the perspective of the milling device 10. Thus, "proximal" refers to the direction of coupling with the attachment tang 17 and "distal" refers to the direction of coupling with the milling tool 11. Consequently, the relative terms "proximal" and "distal" when applied to other components refer to the reference described above.

With particular reference to FIGS. 21-24, in the case of surgical application of the device 10 to the shoulder joint, the rotating rod 22 can be provided, in the head or distal position, with a front milling tip 55 which is outside the milling tool 11. The front milling tip 55 cooperates with the milling tool 11 to create a seating for the prosthetic implant.

The front milling tip 55 can be made in a single piece with the rotating rod 22, in correspondence with its distal end 16, and is therefore integral in rotation with the rotating rod 22. The front milling tip 55 has an axial aperture to allow the passage of the guide rod 50 in the guide channel 42. When the milling tool 11 is driven in rotation and advances removing the bone, at the same time the front milling tip 55 also rotates, thus also making an axial hole in the bone (along the longitudinal axis Z) which houses the part of the rotating rod 22 axially protruding from the milling tool 11. The front milling tip 55, therefore, rotates about an axis coaxial to the longitudinal axis Z, and not about the milling axis R of the milling tool 11. In particular, in this variant described with reference to FIGS. 21-24, the point of intersection of the milling axis R and the longitudinal axis Z falls outside the milling tool 11 (see in particular FIG. 23).

In accordance with some embodiments, the angular joint 18 is positioned in correspondence with or in the proximity of the distal end 16 of the rotating rod 22, and is rotatably coupled to the polar coupling aperture 13 with degrees of freedom able to allow the milling tool 11 to selectively assume a plurality of positions that are inclined with respect to the longitudinal axis Z.

In accordance with some embodiments, the handling body 14 comprises the tubular handle 23 which is coaxially coupled, in a removable manner, with the rotating rod 22 and is provided with the positioning member 20.

The tubular handle 23 is provided with a distal aperture 25 and with a proximal aperture 26, respectively associated with the distal end 16 and the proximal end 15 of the rotating rod 22.

The tubular handle 23 has a longitudinal channel 27 made through from the distal aperture 25 to the proximal aperture 26 for the rotational coupling with the rotating rod 22. Advantageously, the longitudinal channel 27 has a size in a direction orthogonal to the longitudinal axis Z which is greater than that of the rotating rod 22, thus allowing to prevent unwanted sliding.

In accordance with possible solutions, the tubular handle 23 can be made in a single piece or it can be made in two separate parts which can be selectively joined in order to form a shell to house the rotating rod 22. Advantageously, the tubular handle 23 can be made of plastic material in order to reduce possible friction with the rotating rod 22 and with the milling tool 11 to a minimum.

In accordance with the embodiments described here, with particular reference to FIGS. 8-9, and FIG. 13 and FIG. 17, and which can be combined with all the other embodiments described, the size of the proximal aperture 26 is slightly smaller than the size of the longitudinal channel 27 in order to cooperate with a retaining edge, or tooth 30, for example circumferential, of the rotating rod 22 and guarantee a desired positioning of the rotating rod 22 in the direction of the longitudinal axis Z. The retaining edge 30 allows the snap-in attachment of the tubular handle 23 onto the rotating rod 22.

Advantageously, the tubular handle 23 can have, externally, an ergonomic and non-slip grip 28 so that it is easier for the user to grip and handle it. For this purpose, the tubular handle 23 has longitudinal grooves 29 which extend at least in a central zone thereof, possibly having knurled surfaces. In addition, the grip 28 can have a camber in order to further improve the grip.

Advantageously, in some embodiments, see for example FIGS. 26, 27, 31, 32, 34, 37-46, and which can be combined with all the embodiments described here, the tubular handle 23 can have, or be associated with, a safety clamping nut 58. The safety clamping nut 58 secures the tubular handle 23 along the longitudinal axis Z in order to prevent the tubular handle 23 from being accidentally released, during the surgical act, due to pressure on it.

The positioning member 20 and in particular the stabilizing body 21 is configured to cooperate with the concave coupling seating 12.

In accordance with some embodiments, the stabilizing body 21 is configured to make a same-shape coupling with the concave coupling seating 12 of the milling tool 11 so as to define the above described specific stable inclined position of the milling tool 11 with respect to the longitudinal axis Z based on the eccentricity with respect to the longitudinal axis Z.

The positioning member 20 comprises the distal aperture 25 and a sliding coupling seating 31 configured to house a shaped portion 40 of the rotating rod 22 in order to guarantee a desired positioning of the rotating rod 22 in the direction of the longitudinal axis Z. In particular, the seating 31 is concentric with respect to the longitudinal axis Z.

The seating 31 is configured to exert an action of positioning the rotating rod 22 in cooperation with the positioning action exerted by the retaining edge 30. In this way, once the rotating rod 22 is operatively inserted in the longitudinal channel 27, its positioning in the direction of the longitudinal axis Z is substantially determined. In particular, the shaped portion 40 is in rotational coupling with the seating 31. This coupling presupposes that there is a minimum space between the surfaces of the seating 31 and the surfaces of the shaped portion 40, so as to allow the functional movement.

Figure 2:
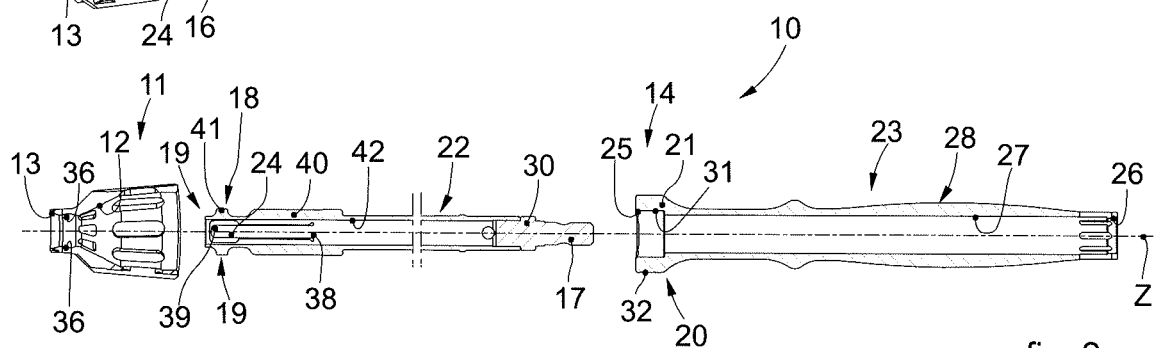
FIG. 2 shows a lateral elevation section view of FIG. 1.
Figure 3:
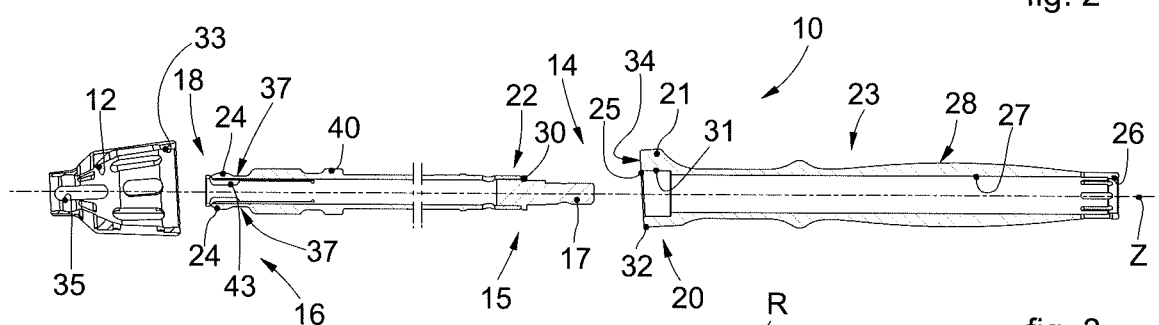
FIG. 3 shows another lateral elevation section view of FIG. 1.
Figure 10:
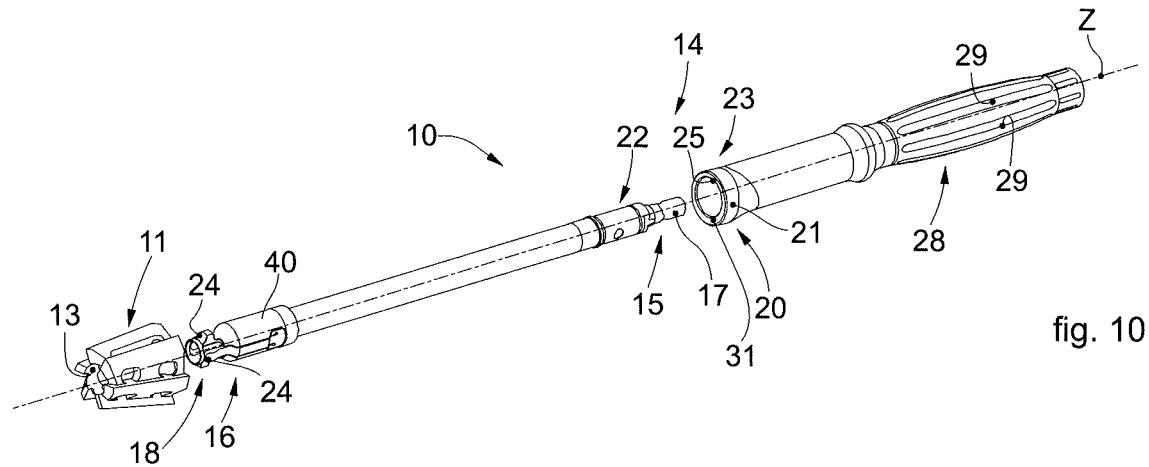
FIG. 10 shows an exploded perspective view of a milling device for prosthetic surgery, in particular for application to the femoral bone, in accordance with some embodiments described here.
Figure 11:
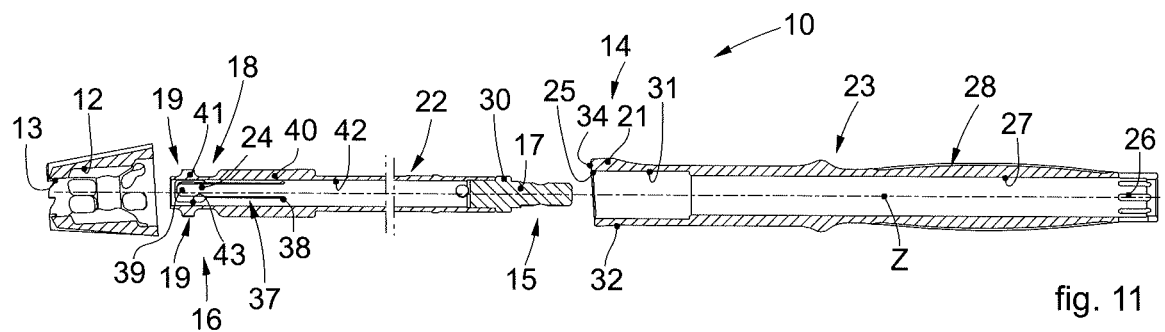
FIG. 11 shows a lateral elevation section view of FIG. 10.
Figure 12:
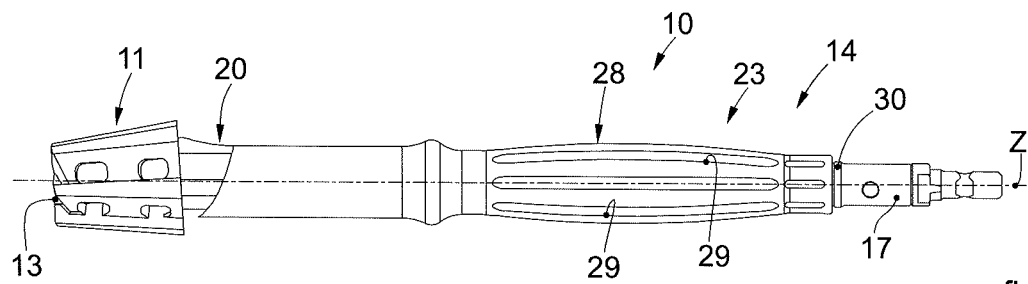
FIG. 12 shows a lateral view of a milling device for prosthetic surgery, in particular for application to the femoral bone, in accordance with some embodiments described here.
Figure 13:
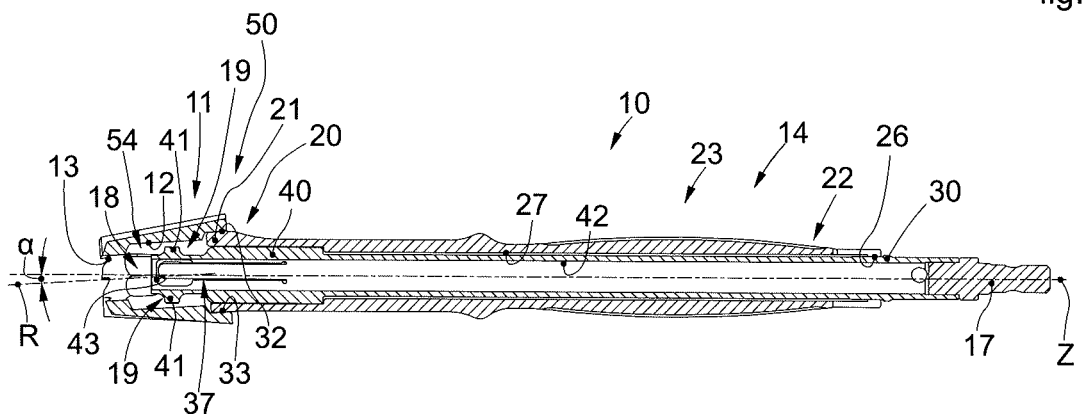
FIG. 13 is a longitudinal section of FIG. 12.

In accordance with some embodiments, for example shown in FIGS. 1-3 and in FIGS. 10-11, the shaped portion 40 has a substantially cylindrical shape.

In some embodiments, see for example FIGS. 1-3, 6-9, 10-13, 14-20, 37-39, 43-46 it can be provided that the stabilizing body 21 is coupled with the inside of the milling tool 11, that is that the stabilizing body 21 acts as a male element for coupling with a respective female seating of the milling tool 11. In other embodiments, as explained in detail below, a mechanical inversion can be provided in the coupling between the stabilizing body 21 and the milling tool 11 (for example FIGS. 40-42).

In some embodiments, see for example FIGS. 1-3, 8-9, 10-13, 18-19, 38-39, the stabilizing body 21 has an external surface 32 coupled slidingly with an internal surface 33 of the concave coupling seating 12 of the milling tool 11. The external surface 32 is defined by a cylindrical portion and is inclined with respect to the longitudinal axis Z by an angle of inclination α that substantially defines the angle of the milling axis R with respect to the longitudinal axis Z. The internal surface 33 of the concave coupling seating 12 has an advantageously cylindrical profile having a diameter slightly larger than the diameter of the cylindrical portion that defines the external surface 32, in order to guarantee the sliding coupling as above. This sliding coupling guarantees the single specific stable inclined position of the milling tool 11 with respect to the longitudinal axis Z.

The external surface 32 and the internal surface 33 are, for example, defined by two cylindrical and concentric portions, which can have an arc with an amplitude even smaller than 180°.

The stabilizing body 21 also has a base surface 34 provided with the distal aperture 25, which allows access to the seating 31. The surface of the seating 31 and the external surface 32 are connected to the base surface 34, the first externally, the second internally with respect to the distal aperture 25. In particular, since the stabilizing body is disposed eccentric with respect to the longitudinal axis Z, the distal aperture 25 is not centered with respect to the base surface 34, but is concentric with the longitudinal axis Z.

Figure 4:
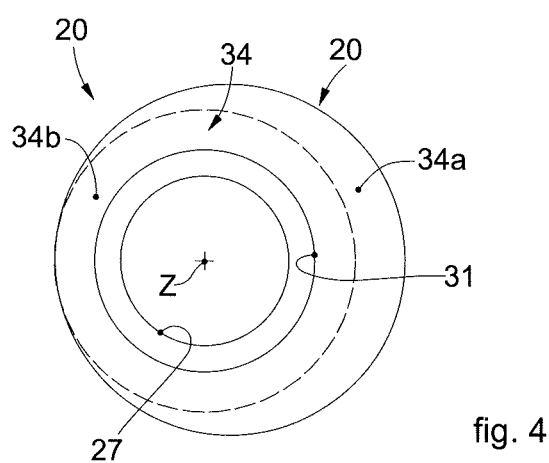
FIG. 4 shows a schematic top plan view of a component of FIG. 1.

As shown schematically in FIG. 4, and also valid for the corresponding embodiments in which it is provided, the base surface 34 is altogether eccentric with respect to the longitudinal axis Z and is defined by a first portion 34a, delimited for illustrative purposes only with a dashed line, which is concentric with respect to the longitudinal axis Z, and by a second portion 34b which is eccentric with respect to the longitudinal axis Z, these portions 34a, 34b essentially being one a continuation of the other. The greater the second portion 34b, and therefore the greater the eccentricity of the base surface 34, the greater the angle of inclination of the milling tool 11 with respect to the longitudinal axis Z in the stable inclined position as above.

The base surface 34 is inclined with respect to the longitudinal axis Z by an angle of inclination α which corresponds to the angle of inclination α of the single specific stable inclined position of the milling tool 11 with respect to the longitudinal axis Z. In the case of a milling device 10 for the preparation of a bone seating for a knee joint prosthesis, the angle of inclination α is between about 7° and 15° (in this case, for example, in the operative variant with bilobed milling, see FIGS. 25-29) for the milling device 10 for the tibial bone, and is about 4° for the milling device 10 for the femoral bone.

Figure 14:
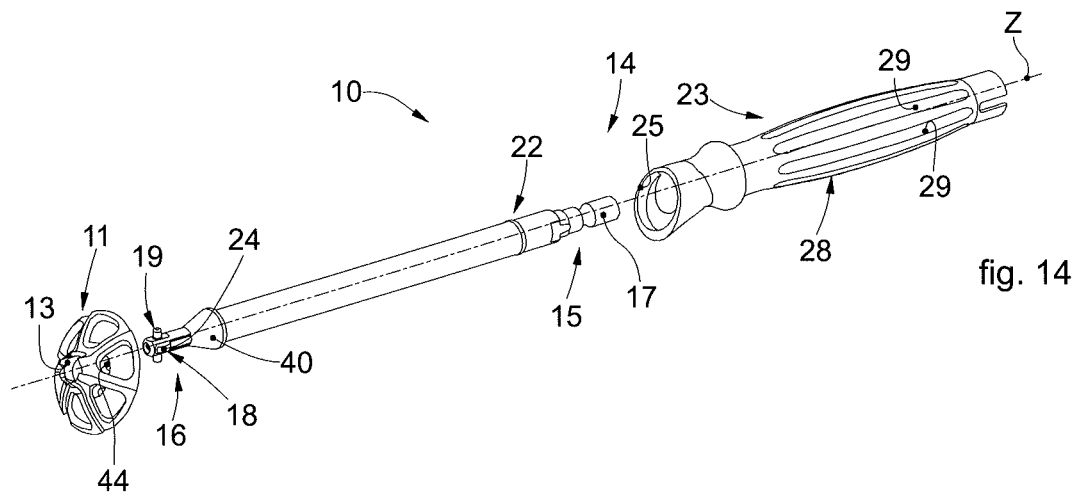
FIG. 14 shows an exploded perspective view of a milling device for prosthetic surgery, in particular for application to the shoulder joint, in particular for the glenoid, in accordance with some embodiments described here.
Figure 15:
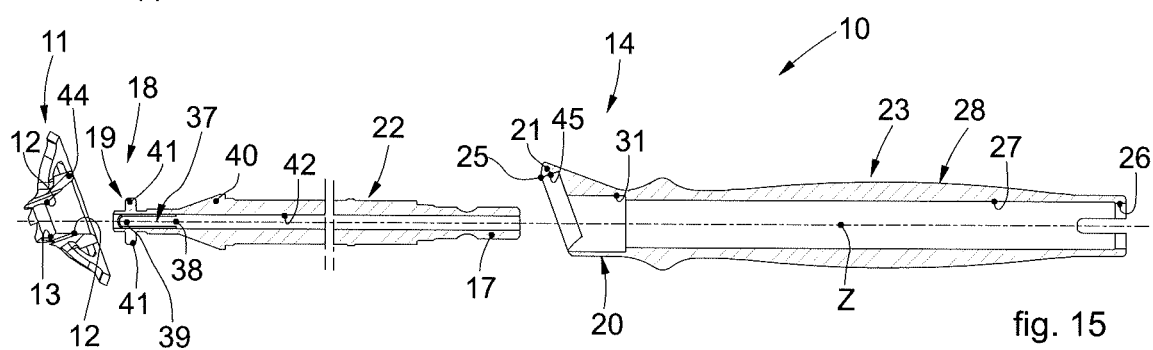
FIG. 15 shows a lateral elevation section view of FIG. 14.
Figure 16:
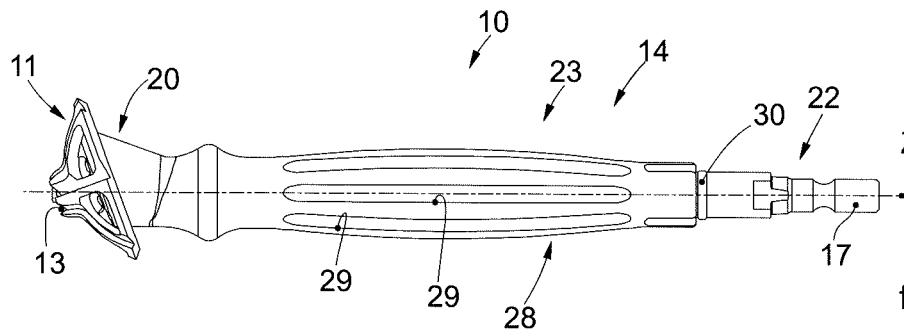
FIG. 16 shows a lateral view of a milling device for prosthetic surgery, in particular for application to the shoulder joint, in particular for the glenoid, in accordance with some embodiments described here.
Figure 17:
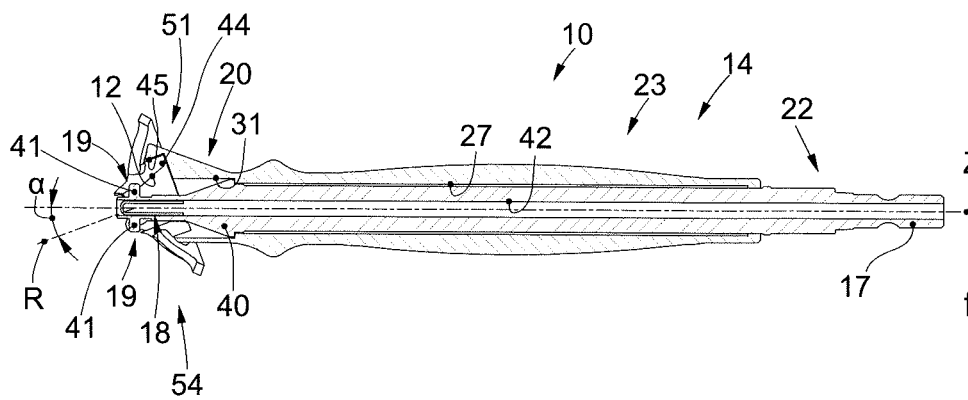
FIG. 17 is a longitudinal section of FIG. 16.
Figure 21:
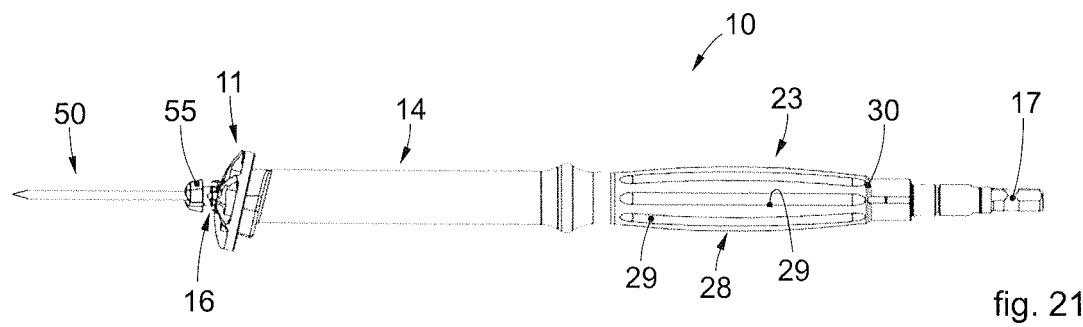
FIG. 21 shows a lateral view of a milling device for prosthetic surgery, in particular for application to the shoulder joint, in particular for the glenoid, in accordance with some embodiments described here.
Figure 22:
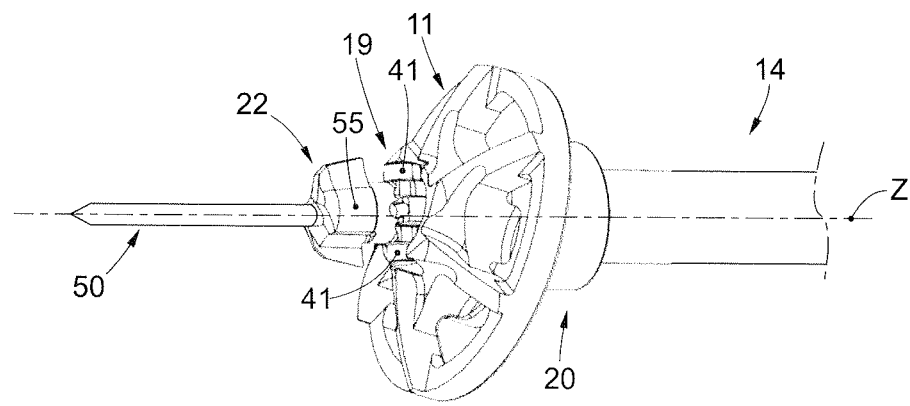
FIG. 22 shows an enlarged detail of FIG. 21.

In accordance with some embodiments, shown in FIGS. 14-15, the shaped portion 40 can have a substantially conical shape.

Also, in some embodiments described using FIGS. 14-20, 21-24 and 40-42, the milling tool 11 is provided with a central body 44 coupled slidingly with a seating 45 of the positioning member 20. This seating 45 can for example be inclined by an angle of inclination α which corresponds to the angle of inclination α of the single specific stable inclined position of the milling tool 11 with respect to the longitudinal axis Z. The concave coupling seating 12 is defined inside the central body 44. Both the seating 45, and also the central body 44 are eccentric with respect to the longitudinal axis Z. This sliding coupling guarantees the single specific stable inclined position of the milling tool 11 with respect to the longitudinal axis Z. In the case of a milling device 10 for the preparation of a bone seating for a shoulder joint prosthesis, in particular for the glenoid, the angle of inclination α can be selected, as needed, so that it is greater than 0° and up to about 25°.

In the embodiments described using FIGS. 14-20, 21-24 in which the seating 45 is provided, the latter has an internal surface 56 coupled slidingly with an external surface 57 of the central body 44 of the concave coupling seating 12 of the milling tool 11. This internal surface 56 is defined by a cylindrical portion and is inclined with respect to the longitudinal axis Z by an angle of inclination α which substantially defines the angle of the milling axis R with respect to the longitudinal axis Z. The external surface 57 of the central body 44 of the concave coupling seating 12 has a cylindrical profile having a diameter slightly smaller than the diameter of the cylindrical portion that defines the internal surface 56. The internal surface 56 and the external surface 57 are, for example, defined by two cylindrical and concentric portions, which can have an arc with an amplitude even smaller than 180°.

In accordance with some embodiments, described using FIGS. 21-24, the shaped portion 40 has a substantially cylindrical shape and has a convex upper articulation surface 52 which develops around the body of the rotating rod 22. The central body 44 has a concave lower articulation surface 53 coupled slidingly, alternatively during the rotation, with the seating 45 and with the upper articulation surface 52. The upper 52 and lower articulation surfaces 53 define the articulation means 54. In the embodiments of FIGS. 21-24, this coupling therefore configures a ball joint having the function of a joint, which is disposed outside the milling tool 11, differently for example from the variant of FIGS. 14-17 in which the joint, see the convex portions 24 of the angular joint 18 described in detail below, is actually disposed inside the milling tool 11. Advantageously, this joint, disposed outside the milling tool 11, reduces the risk of wear and deterioration of the components during milling operations. In particular, the radii of curvature of the upper 52 and lower articulation surfaces 53 are the same. Furthermore, during use, the centers of these radii of curvature have to be coinciding with each other and coinciding with the center of rotation positioned on the longitudinal axis Z in a central position between anti-rotation constraint elements 19 that transmit the rotation. In this case, the center of rotation is outside the milling tool 11. In particular, in this variant described with reference to FIGS. 21-24, the point of intersection of the milling axis R and the longitudinal axis Z falls outside the milling tool 11 (see in particular FIG. 23).

In other embodiments, see for example FIGS. 40-42, it can be provided that the stabilizing body 21 is coupled with the outside of the milling tool 11, that is that the milling tool 11 acts as a male element for coupling with a respective female seating of the stabilizing body 21.

In particular, this can be described with reference to the embodiments of FIGS. 40-42, in which the positioning member 20 has a seating 45 as described above, which, however, does not couple with a central body 44 inside the concave coupling seating 12 of the milling tool 11, but rather couples outside the milling tool 11.

In these embodiments, described by way of example with reference to the variant for interventions to the tibial bone, the stabilizing body 21 has an internal surface 63, in particular with an annular conformation and delimiting the seating 45, and in a mating manner the milling tool 11 has an external surface 62 able to produce a sliding coupling with the internal surface 63.

The internal surface 63 is advantageously defined by a cylindrical portion and is inclined with respect to said longitudinal axis Z by an angle of inclination α which substantially defines the angle of the milling axis R with respect to the longitudinal axis Z.

The external surface 62 has a cylindrical profile having a slightly smaller diameter than the diameter of the cylindrical portion which defines the internal surface 63.

The external surface 62 and the internal surface 63 are, for example, defined by two cylindrical and concentric portions, for example with an arc with an amplitude even smaller than 180°.

In accordance with some embodiments, the anti-rotation constraint elements 19 are present on the distal end 16 of the rotating rod 22 and are operatively coupled with coupling seatings 35 provided in the concave seating 12 of the milling tool 11. The anti-rotation constraint elements 19 are configured to angularly constrain the milling tool 11 with respect to the handling body 14 so that they are able to rotate integrally about the longitudinal axis Z. The anti-rotation constraint elements 19 are configured as means for transmitting torque, from the rotating rod 22 to the milling tool 11.

The anti-rotation constraint elements 19 comprise rigid transmission tongues 41 with a shape mating with corresponding coupling seatings 35 present on the milling tool 11, for the transmission of the rotational motion to the milling tool 11.

The anti-rotation constraint elements 19 protrude radially from the profile of the rotating rod 22, advantageously in a diametrically opposite position to each other if they are present in a number greater than one. Advantageously, in fact, the anti-rotation constraint elements 19 are two, in order to guarantee a better transmission of the rotation torque from the rotating rod 22 to the milling tool 11. This diametrically opposite disposition of the two anti-rotation constraint elements 19 allows the milling tool 11 to oscillate or rotate on a plane orthogonal to the one passing through the anti-rotation constraint elements 19, in such a way as to selectively assume a plurality of positions that are inclined with respect to the longitudinal axis Z, and in particular to assume a single specific stable inclined position defined by the same-shape coupling of the stabilizing body 21 with the concave coupling seating 12 of the milling tool 11.

The anti-rotation constraint elements 19 are removably keyed into the coupling seatings 35, made in correspondence with the polar coupling aperture 13 of the milling tool 11.

The coupling seatings 35 are substantially radial with respect to the longitudinal axis Z and are configured to guarantee the constraint necessary for the transmission of the rotation torque from the rotating rod 22 to the milling tool 11.

Advantageously, the coupling seatings 35 are in a number coherent with the number of anti-rotation constraint elements 19. This guarantees a unique and determinate connection of the milling tool 11 onto the rotating rod 22, preventing possible assembly errors.

In the embodiments described using FIGS. 21-24, in which the front milling tip 55 is provided and the point of intersection of the milling axis R and the longitudinal axis Z falls outside the milling tool 11, the risk of wear and deterioration of the transmission tongues 41 is advantageously reduced, since the torque necessary for the milling and the torque necessary to create the seating of the spherical cap during the forward movement does not have to come exclusively from the transmission tongues 41, but part of the milling action is performed by the cutting edges of the front milling tip 55 which is integral with, and made in a single piece on, the rotating rod 22 of the handling body 14 and, therefore, act independently of the milling tool 11.

In accordance with some embodiments, the angular joint 18 has one or more convex curved portions 24 disposed around the longitudinal axis Z.

Advantageously, the angular joint 18 has at least two convex curved portions 24 disposed diametrically opposite each other with respect to the longitudinal axis Z.

In accordance with the embodiments described here, the anti-rotation constraint elements 19 are disposed around the longitudinal axis Z alternating with the convex curved portions 24.

The convex curved portions 24 protrude radially from the profile of the rotating rod 22 in a diametrically opposite position with respect to that of the anti-rotation constraint elements 19 and are configured to couple with respective shaped concavities 36, having a shape mating with that of the convex curved portions 24.

Advantageously, the shaped concavities 36 allow an elastic snap-in coupling that univocally determines the axial position of the milling tool 11. In fact, when the milling tool 11 is coupled with the rotating rod 22, the convex curved portions 24 are removably forced to associate with the shaped concavities 36.

Advantageously, the one or more convex curved portions 24 are sphere portions.

In accordance with some embodiments, the angular joint 18 comprises elastic keying tongues 37 each provided with one of the convex curved portions 24, for example conformed as a hemispherical portion (see for example FIGS. 1, 3, 10, 11, 14, 24).

Each keying tongue 37 has an extension in the direction of the longitudinal axis Z and has a tip 39 provided with the convex curved portion 24, and a base 38, opposite the tip 39, stably attached to the rotating rod 22. Advantageously, only the base 38 is stably attached to the rotating rod 22 so that the keying tongue 37 can flex with respect to the base 38 when a pressure is exerted on the tip 39.

The keying tongue 37 can flex in a direction orthogonal to the longitudinal axis Z. For this purpose, the angular joint 18 has a chamber 43, FIG. 3 and FIG. 11, made through orthogonally in the rotating rod 22 and configured to allow the inward flexion of the keying tongues 37, at least during the coupling with the milling tool 11.

In accordance with some embodiments, shown in FIGS. 25-29, a possible operating sequence of use of the milling tool 10 for surgical application to the tibial bone is shown. In the example described here, there is shown an operating sequence to obtain a "bilobed" type milling, useful in the event that the degeneration of the spongy part of the bone is rather extensive. In fact, in this case it is more appropriate to mill with a smaller milling tool 11, performing a double milling as described below. However, the same procedure can be applied to produce a single milling, for example using a milling tool 11 of larger sizes.

After having performed the proximal resection of the tibial bone, perpendicular to the intra-medullary axis, a reaming tool is used that allows to define, possibly with several passes with increasing diameter, a lead-in channel 111 for the milling tool 11, FIG. 25. Advantageously, the part of the reaming tool that does not have the cutting edges remains protruding from the resection plane and acts as a guide rod 50 for the milling tool 11.

Once the lead-in channel 111 has been made, the milling tool 11 is positioned vertically so that the longitudinal axis Z is aligned with the axis of development of the guide rod 50, and moved closer to it so that the guide rod 50 couples slidingly in the guide channel 42 of the rotating rod 22.

At this point, since the milling is asymmetrical, it is possible to define a right milling, in which the angle of inclination α with respect to the longitudinal axis Z has a positive value (FIG. 26), and a left milling, in which the angle of inclination α with respect to the longitudinal axis Z has a negative value (FIG. 27).

What is obtained is a seating that is substantially symmetrical with respect to a central (sagittal) plane transverse to the previously prepared lead-in channel 111, and equidistant from the cortical zone 110 of the bone, FIGS. 28-29. This solution allows to simplify and speed up the milling operation for the preparation of such a seating 112 for a bone filler, and to avoid breaking the cortical zone of the bone in the event of extensive bone gaps following the failure of previous implants.

FIGS. 30-33 are used to describe a possible operating sequence of use of a milling device 10 provided with a milling tool 11 for surgical application to the femoral bone. FIG. 30 shows the use of the reaming tool to create the guide channel 111 in the femoral bone. Also in this case, the guide rod 50 corresponding to the part of the reaming tool that remains protruding from the resection plane is indicated. After that, FIG. 31, the milling tool 11 is coupled with the guide rod 50. The latter, therefore, is aligned with the longitudinal axis Z, while the milling tool 11 is inclined along the respective milling axis R. FIG. 32 shows the milling operation, where it can be clearly seen that the milling has an angle of inclination α with respect to the longitudinal axis Z. FIG. 33 shows the seating 112 thus obtained, once the milling device 10 has been removed.

It is clear that modifications and/or additions of parts may be made to the guided milling device for prosthetic surgery as described heretofore, without departing from the field and scope of the present invention as defined by the claims.

It is also clear that, although the present invention has been described with reference to some specific examples, a person of skill in the art shall certainly be able to achieve many other equivalent forms of a guided milling device for prosthetic surgery, having the characteristics as set forth in the claims and hence all coming within the field of protection defined thereby.

In the following claims, the sole purpose of the references in brackets is to facilitate reading and they must not be considered as restrictive factors with regard to the field of protection claimed in the specific claims.

The invention claimed is:

1. Guided milling device for prosthetic surgery for creating glenoid seatings for shoulder joint prostheses, said device comprising:
a milling tool rotating about a milling axis;
a handling body having a drive rotating rod which develops along a longitudinal axis of linear rotation, connected to said milling tool in order to make said milling tool rotate about said milling axis;
wherein said rotating rod is internally hollow and has a guide channel parallel to the longitudinal axis in which a guide rod is housed coaxially in a slidable manner, able to be positioned to extend beyond said milling tool along said longitudinal axis,
wherein said milling axis is inclined with respect to said longitudinal axis, so that said milling tool is disposed inclined with respect to said rotating rod and also to said guide rod,
wherein the point of intersection of the milling axis and of the longitudinal axis falls outside the milling tool.

2. Device as in claim 1, wherein said rotating rod is provided, in the head or distal position, with a front milling tip outside the milling tool.

3. Device as in claim 1, wherein it comprises an angular positioning assembly configured to define the inclined disposition of said milling tool with respect to said guide rod and said rotating rod.

4. Device as in claim 3, wherein said angular positioning assembly comprises articulation means to connect said milling tool to said rotating rod in an articulated manner, allowing to selectively define a plurality of inclined positions of said milling tool with respect to said longitudinal axis, and a positioning member which comprises a stabilizing body disposed eccentric with respect to said longitudinal axis, configured to cooperate with said milling tool so as to selectively define, from among said plurality of inclined positions, a single specific stable inclined position of said milling tool in which said milling tool is able to rotate along said milling axis inclined with respect to said longitudinal axis.

5. Device as in claim 4, wherein said handling body comprises said positioning member.

6. Device as in claim 4, wherein said stabilizing body is configured to make a same-shape coupling with said milling tool so as to define said single specific stable inclined position of said milling tool with respect to said longitudinal axis, based on the eccentricity with respect to said longitudinal axis.

7. Device as in claim 4, wherein said handling body comprises a tubular handle coaxially coupled in a removable manner to said rotating rod and comprising said positioning member.

8. Device as in claim 4, wherein said articulation means comprise an angular joint rotatably coupled with said milling tool.

9. Device as in claim 8, wherein said angular joint has one or more convex curved portions disposed around said longitudinal axis.

10. Device as in claim 9, wherein said one or more convex curved portions are sphere portions.

11. Device as in claim 9, wherein said angular joint has at least two convex curved portions disposed diametrically opposite with respect to said longitudinal axis.

12. Device as in claim 9, wherein said angular joint comprises elastic keying tongues, each provided with one of said convex curved portions.

13. Device as in claim 4, wherein said stabilizing body has a seating having an internal surface coupled slidingly with an external surface of the central body of the concave coupling seating of the milling tool.

14. Device as in claim 13, wherein said internal surface is defined by a cylindrical portion and is inclined with respect to said longitudinal axis by an angle of inclination which substantially defines the angle of said milling axis with respect to the longitudinal axis.

15. Device as in claim 13, wherein said external surface of the central body of the concave coupling seating has a cylindrical profile with a diameter slightly smaller than the diameter of said cylindrical portion that defines said internal surface.

16. Device as in claim 4, wherein said articulation means comprise respective curved articulation surfaces provided on said rotating rod and on said milling tool.

17. Device as in claim 4, wherein the stabilizing body is coupled outside the milling tool.

18. Device as in claim 1, wherein said milling tool has a concave coupling seating having a polar coupling aperture, said rotating rod being provided with a distal end connected to the milling tool in correspondence with, or in the proximity of, the polar coupling aperture, said distal end being open in order to allow the insertion of the guide rod into said guide channel.

19. Device as in claim 18, wherein it comprises anti-rotation constraint elements present on said distal end of said rotating rod, operatively coupled with coupling seatings provided inside said concave coupling seating.

20. Device as in claim 19, wherein said anti-rotation constraint elements are disposed around said longitudinal axis alternating with said convex curved portions.

21. Device as in claim 19, wherein said anti-rotation constraint elements comprise rigid transmission tongues with a shape mating with corresponding coupling seatings present on said milling tool, in order to transmit the rotational motion to the milling tool.

* * * * *